(12) United States Patent
Tung (10) Patent No.: US 7,932,235 B2
(45) Date of Patent: Apr. 26, 2011

(54) TRIAZOLYL TROPANE DERIVATIVES

(75) Inventor: Roger Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 142 days.

(21) Appl. No.: 11/941,925

(22) Filed: Nov. 16, 2007

(65) Prior Publication Data

US 2008/0161264 A1 Jul. 3, 2008

Related U.S. Application Data

(60) Provisional application No. 60/859,881, filed on Nov. 17, 2006.

(51) Int. Cl.
*A61K 31/46* (2006.01)
*A61K 31/7068* (2006.01)
*C07D 451/02* (2006.01)
*A61P 31/18* (2006.01)

(52) U.S. Cl. ............ 514/49; 514/50; 514/304; 546/125
(58) Field of Classification Search ............. 514/50, 514/49, 304; 546/125
See application file for complete search history.

(56) References Cited

U.S. PATENT DOCUMENTS

| | | | |
|---|---|---|---|
| 5,846,514 A | 12/1998 | Foster et al. | |
| 6,221,335 B1 | 4/2001 | Foster | |
| 6,440,710 B1 | 8/2002 | Keinan et al. | |
| 6,603,008 B1 | 8/2003 | Ando et al. | |
| 6,667,314 B2 * | 12/2003 | Perros et al. | 514/304 |
| 7,517,990 B2 | 4/2009 | Ito et al. | |
| 2007/0082929 A1 | 4/2007 | Gant et al. | |
| 2007/0197695 A1 | 8/2007 | Potyen et al. | |
| 2008/0103122 A1 | 5/2008 | Veltri | |
| 2008/0146605 A1 | 6/2008 | Gant et al. | |

FOREIGN PATENT DOCUMENTS

| | | |
|---|---|---|
| WO | WO-95/26325 | 10/1995 |
| WO | WO-01/90106 | 11/2001 |
| WO | WO-03/084954 | 10/2003 |

OTHER PUBLICATIONS

Koenig et al., Biochemistry, 1999, vol. 38, pp. 6327-6334.*

Price et al., "Initial synthesis of UK-427,857 (Maraviroc)", Tetrahedron Letters 46 (2005), pp. 5005-5007.
Hughes, et al., "New antiretroviral drugs: a review of the efficacy, safety, pharmacokinetics, and resistance profile of tipranavir, darunavir, etravirine, rilpivirine, maraviroc, and raltegravir", Expert Opinion Pharmacother (2009), 10 (15), pp. 1-22.
Walker, et al., "Species differences in the disposition of the CCR5 antagonist, UK-427,857, a new potential treatment for HIV", Drug Metabolism and Disposition, vol. 33, No. 4, 2005, pp. 587-595.
Kushner, D.J. et al: "Pharmacological Uses and Perspectives of Heavy Water and Deuterated Compounds," Can. J. Physiol. Pharmacol 77: 79-88 (1999).
International Search Report in corresponding PCT International Application No. PCT/US2007/024167.
International Preliminary Report on Patentability in corresponding PCT International Application No. PCT/US2007/024167.
Browne, T.R., Journal of Clinical Pharmacology 38: 213-220 (1998).
Baillie, T.A., Pharmacology Rev. 33:81-132 (1981).
Gouyette, A., Biomedical and Environmental Mass Spectrometry, vol. 15, 243-247 (1988).
Cherrah, Y. et al., Biomedical and Environmental Mass Spectrometry, vol. 14, Issue 11, pp. 653-657 (1987).
Dyck, L.E. et al., Journal of Neurochemistry, vol. 46, Issue 2, pp. 399-404 (1986).
Tonn, G.R., et al., Biological Mass Spectrometry, vol. 22, Issue 11, pp. 633-642 (1993).
Haskins, N.J., Biomedical Spectrometry, vol. 9, Issue 7, pp. 269-277 (1982).
Wolen, R.L., J. Clin. Pharmacology 26: 419-424 (1986).
Pieniaszek, H.J. et al., J. Clin. Pharmacol. 39:817-825 (1999).
Honma, S. et al., Drug Metab Dispos 15(4): 551 (1987).
Foster, A.B., Adv Drug Res, 14:1-40 (1985).
Fisher, M.B. et al., Current Opinion in Drug Discovery & Development 9:101-09 (2006).
Foster, A.B., "Deuterium isotope effects in studies of drug metabolism", TIPS 524-527 (Dec. 1984).

* cited by examiner

*Primary Examiner* — D. Margaret Seaman
*Assistant Examiner* — Niloofar Rahmani
(74) *Attorney, Agent, or Firm* — Edwards Angell Palmer & Dodge LLP; Jeffrey D. Hsi; Mark D. Russett (57) ABSTRACT

This invention relates to novel triazolyl tropane derivatives, their acceptable acid addition salts, solvates, hydrates and polymorphs thereof. The invention also provides compositions comprising a compound of this invention and the use of such compositions in methods of treating diseases and conditions beneficially treated by blocking or reducing the binding ability of the CCR5 receptor.

9 Claims, 1 Drawing Sheet

*FIG. 1*

TRIAZOLYL TROPANE DERIVATIVES

CROSS-REFERENCE TO RELATED APPLICATIONS

This application claims the benefit of U.S. Provisional Patent Application No. 60/859,881, filed Nov. 17, 2006, the contents of which are incorporated herein by reference in their entirety.

TECHNICAL FIELD OF THE INVENTION

This invention relates to novel triazolyl tropane derivatives. The invention also provides compositions comprising a compound of this invention and the use of such compositions in methods of treating diseases and conditions beneficially treated by blocking or reducing the binding ability of the CCR5 receptor.

BACKGROUND OF THE INVENTION

Maraviroc, chemically described as N-{(1S)-3-[3-(3-Isopropyl-5-methyl-4H-1,2,4-triazol-4-yl)-exo-8-azabicyclo[3.2.1]oct-8-yl]-1-phenylpropyl}-4,4-difluorocyclohexanecarboxamide or 4,4-difluoro-N-{(1S)-3-[exo-3-(3-isopropyl-5-methyl-4H-1,2,4-triazol-4-yl)-8-azabicyclo[3.2.1]oct-8-yl]-1-phenylpropyl}cyclohexanecarboxamide and its pharmaceutically acceptable addition salts and hydrates thereof, are disclosed as modulators of the chemokine receptor CCR5 and thus useful in the treatment of retroviral diseases caused by viruses that utilize CCR5 to enter cells. In particular maraviroc has been disclosed as being a useful therapeutic in the treatment of HIV, a retroviral infection genetically related to HIV, AIDS, or an inflammatory disease (see U.S. Pat. No. 6,667,314). Maraviroc is presently undergoing investigative human clinical trials [Bayes M et al., Methods Find Exp Clin Pharmacol 2003 25:145-68].

Additional diseases and conditions that can be treated with maraviroc include respiratory disorders, including adult respiratory distress syndrome (ARDS), bronchitis, chronic bronchitis, chronic obstructive pulmonary disease, cystic fibrosis, asthma, emphysema, rhinitis and chronic sinusitis. Other conditions that may be treated are those triggered, affected or are in any other way correlated with T-cell trafficking in different organs and for which a correlation with CCR5 or CCR5 chemokines has been established. These are inflammatory bowel disease, including Crohn's disease and ulcerative colitis, multiple sclerosis, rheumatoid arthritis, graft rejection, in particular but not limited to kidney and lung allografts, endometriosis, type I diabetes, renal diseases, chronic pancreatitis, inflammatory lung conditions or chronic heart failure.

Despite the beneficial activities of maraviroc, there is a continuing need for new compounds to treat the aforementioned diseases and conditions.

DEFINITIONS

The terms "ameliorate" and "treat" are used interchangeably and both mean decrease, suppress, attenuate, diminish, arrest, or stabilize the development or progression of a disease (e.g., a psychotic disorder).

By "disease" is meant any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of maraviroc will inherently contain small amounts of deuterated and/or $^{13}$C-containing isotopologues. The concentration of naturally abundant stable hydrogen and carbon isotopes, notwithstanding this variation, is small and immaterial with respect to the degree of stable isotopic substitution of compounds of this invention. See for instance Wada E and Hanba Y, Seikagaku 1994 66:15; Ganes L Z et al., Comp Biochem Physiol A Mol Integr Physiol 1998 119:725. The compounds of the present invention are distinguished from such naturally occurring minor forms in that the term "compound" as used in this invention refers to a composition of matter that is predominantly a specific isotopologue.

In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3000 (45% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

The term "isotopologue" refers to a species that differs from a specific compound of this invention only in the isotopic composition thereof.

In certain embodiments, a compound of this invention contains less than 10%, preferably less than 6%, and more preferably less than 3% of all other isotopologues combined, including a form that lacks any deuterium or $^{13}$C. In certain aspects, the compound contains less than "X" % of all other isotopologues combined, including a form that lacks any deuterium or $^{13}$C; where X is any number between 0 and 10 (e.g., 1, 0.5, 0.001), inclusive. Compositions of matter that contain greater than 10% of all other isotopologues combined are referred to herein as "mixtures" and must meet the parameters set forth below. These limits of isotopic composition and all references to isotopic composition herein, refer solely to the relative amounts of deuterium/hydrogen and $^{13}$C/$^{12}$C present in the active, free base form of the compound of Formula I, and do not include the isotopic composition of hydrolyzable portions of prodrugs, or of counterions.

The term "isotopologue" refers to species that differ from a specific compound of this invention only in the isotopic composition of their molecules or ions.

The term "compound" as used herein, is also intended to include salts, prodrugs, and prodrug salts of a compound of formulae herein. The term also includes any solvates, hydrates, and polymorphs of any of the foregoing. The specific recitation of "prodrug," "prodrug salt," "solvate," "hydrate," or "polymorph" in certain aspects of the invention described in this application shall not be interpreted as an intended omission of these forms in other aspects of the invention where the term "compound" is used without recitation of these other forms.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present invention contain one or more asymmetric carbon atoms. As such, a compound of this invention can exist as the individual stereoisomers (enantiomers or diastereomers) as well a mixture of stereoisomers. Accordingly, a compound of the present invention will include not only a stereoisomeric mixture, but also individual respective stereoisomers substantially free from one another stereoisomers. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X" % of other stereoisomers (wherein X is a number between 0 and 100, inclusive) are present. Methods of obtaining or synthesizing diastereomers are well known in the art and may be applied as practicable to final compounds or to starting material or intermediates. Other embodiments are those wherein the compound is an isolated compound. The term "at least X % enantiomerically enriched" as used herein means that at least X % of the compound is a single enantiomeric form, wherein X is a number between 0 and 100, inclusive.

The term "stable compounds", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to atypical antipsychotic agents).

The terms "lighter isotopologue" and "lighter atom isotopologue" as used herein, refer to species that differ from a specific compound of this invention in that they comprise one or more light isotopic atoms ($^1$H or $^{12}$C) at positions occupied by a deuterium or $^{13}$C in the specific compound. For the purposes of this invention, $^{11}$C is not referred to as a light isotope of carbon.

A specific compound of this invention may also be referred to as a "heavy atom isotopic compound" to distinguish it from its lighter isotopologues when discussing mixtures of isotopologues.

The term "heavy atom" refers to isotopes of higher atomic weight than the predominant naturally occurring isotope. The term "stable heavy atom" refers to non-radioactive heavy atoms. "D" refers to deuterium. "Stereoisomer" refers to enantiomers and diastereomers.

Throughout this specification, a variable may be referred to generally (e.g., "each Y") or may be referred to specifically (e.g., $Y^{1a}, Y^{1b}, Y^{2a}, Y^{2b},$ and $Y^{2c}$). Unless otherwise indicated, when a variable is referred to generally, it is meant to include all specific embodiments of that particular variable.

Therapeutic Compounds

The present invention provides a compound of formula I:

(I)

or a salt, hydrate, or solvate thereof; wherein:

$R^1$ is selected from $C_1$-$C_6$ alkyl optionally substituted by one or more fluorine atoms; $C_3$-$C_6$ cycloalkyl optionally substituted by one or more fluorine atoms; and $C_3$-$C_6$ cycloalkylmethyl optionally ring substituted by one or more fluorine atoms, wherein one or more hydrogen atoms in $R^1$ is optionally replaced with deuterium;

$R^2$ is phenyl optionally substituted by one or more fluorine atoms;

each Y (i.e., each of $Y^{1a}, Y^{1b}, Y^{2a}, Y^{2b},$ and $Y^{2c}$) is independently selected from hydrogen or deuterium; and at least one Y is deuterium.

In another embodiment, the present invention provides a compound of formula II:

(II)

or a salt, hydrate, or solvate thereof; wherein:

each Y (i.e., each of $Y^{1a}, Y^{1b}, Y^{2a}, Y^{2b},$ and $Y^{2c}$) is independently selected from hydrogen or deuterium;

each Z is independently selected from hydrogen or deuterium; and at least one Y or one Z is deuterium.

In another embodiment of formula I or formula II, $Y^{2a}, Y^{2b}$ and $Y^{2c}$ are the same. In another embodiment, $Y^{2a}, Y^{2b}$ and $Y^{2c}$ are simultaneously deuterium.

In another embodiment of formula I or formula II, $Y^{1a}$ and $Y^{1b}$ are simultaneously deuterium.

In another embodiment of formula I or formula II, $Y^{1a}, Y^{1b}, Y^{2a}, Y^{2b}$ and $Y^{2c}$ are simultaneously deuterium.

In one specific embodiment of formula II, each Z bound to the same carbon atom is the same. More preferably, each member of at least one pair selected from $Z^1$ and $Z^2$; $Z^3$ and $Z^4$; $Z^5$ and $Z^6$; or $Z^7$ and $Z^8$ is simultaneously deuterium. Even more preferred is when $Y^{2a}, Y^{2b}$ and $Y^{2c}$ also are simultaneously deuterium; or when $Y^{1a}$ and $Y^{1b}$ also are simultaneously deuterium.

In another specific embodiment of formula II, each Z is hydrogen.

In yet another preferred embodiment, the present invention provides a compound of Formula II, selected from any one of the compounds (Cmpd) set forth in the table below:

TABLE 1

Exemplary Embodiments of Formula II

| Cmpd | $Y^{1a}$ | $Y^{1b}$ | $Y^{2a}$ | $Y^{2b}$ | $Y^{2c}$ | $Z^1$ | $Z^2$ | $Z^3$ | $Z^4$ | $Z^5$ | $Z^6$ | $Z^7$ | $Z^8$ |
|---|---|---|---|---|---|---|---|---|---|---|---|---|---|
| 200 | D | D | H | H | H | H | H | H | H | H | H | H | H |
| 201 | H | H | D | D | D | H | H | H | H | H | H | H | H |
| 202 | H | H | H | H | H | D | D | D | D | D | D | D | D |
| 203 | D | D | D | D | D | H | H | H | H | H | H | H | H |
| 204 | D | D | H | H | H | D | D | D | D | D | D | D | D |
| 205 | H | H | D | D | D | D | D | D | D | D | D | D | D |
| 206 | D | D | D | D | D | D | D | D | D | D | D | D | D |
| 207 | H | H | D | D | D | D | D | H | H | H | H | D | D |
| 208 | D | D | H | H | H | D | D | H | H | H | H | D | D |
| 209 | D | D | D | D | D | D | D | H | H | H | H | D | D |
| 210 | D | D | H | H | H | H | H | D | D | D | D | H | H |
| 211 | H | H | D | D | D | H | H | D | D | D | D | H | H |
| 212 | D | D | D | D | D | H | H | D | D | D | D | H | H |

In another set of embodiments, any atom not designated as deuterium in any of the embodiments set forth above is present at its natural isotopic abundance.

In an even more specific embodiment, the compound is selected from:

Compound 200 and

Compound 203

The synthesis of compounds of the formulae herein can be readily effected by synthetic chemists of ordinary skill. Relevant procedures and intermediates are disclosed, for instance, in PCT publication WO 01/90106.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Certain intermediates can be used with or without purification (e.g., filtration, distillation, sublimation, crystallization, trituration, solid phase extraction, and chromatography).

A convenient method for producing compounds of formula I or II involves the synthetic steps shown in the following schemes.

Scheme 1

The starting bicyclic diamine 100 in Scheme 1 is prepared according to methods disclosed in U.S. Pat. No. 6,667,314. The primary amine of 100 is acylated with isobutyric acid and EDC. The amide 101 is then converted to the 1,3,4-triazole 102 by reaction with the appropriately deuterated acetylhydrazide under dehydrating conditions. Transfer catalytic hydrogenolysis removes the benzyl group to provide 103.

Scheme 2

Formula I or II

The synthesis is completed according to steps shown in Scheme 2. The chiral methyl ester 104 is prepared as disclosed in U.S. Pat. No. 6,667,314. The methyl ester is reduced with lithium aluminum deuteride to the deuterated alcohol 105, which is then converted to the mesylate 106 with methanesulfonyl chloride and DIEA in DCM. Alkylation of 103 from Scheme 1 with the mesylate 106 in acetonitrile and DBU provides 107. Cleavage of the Boc protecting group from 107 with HCl followed by neutralization to the free base provides the primary amine 108, which is then acylated with acid chloride 109 to provide compounds of Formula II.

An alternate synthesis for a compound of Formula II is shown in Scheme 3 below.

Ph=phenyl, Bn=benzyl, BOC=tert-butyloxy-carbonyl, MeOH=methanol, EtOH=ethanol, Ac=acetyl, Pyr=pyridine.

2,5-dimethoxytetrahydrofuran (95) is combined with acetone dicarboxylic acid (96) and benzyl amine HCl salt (97) in sodium acetate to give 8-benzyl-8-azabicyclo[3.2.1]octan-3-one 98. The ketone 98 in ethanol is added to hydroxylamine hydrochloride and pyridine, and heated under reflux conditions to afford 8-benzyl-8-azabicyclo[3.2.1]octan-3-one oxime 99. The oxime 99 in 1-pentanol is combined with sodium metal and heated under reflux to produce 8-benzyl-8-azabicyclo[3.2.1]octan-3-amine 100. The amine 100 in $CH_2Cl_2$ (13 mL) is treated with 1M $Na_2CO_3$ and isobutyryl chloride to yield amide 101. The amide 101 is dissolved in $CHCl_3$ and pyridine followed by the addition of $POCl_3$. To this was then added diisopropylethylamine and appropriately deuterated acetylhydrazine 110 to produce triazol 102. The triazole 102 in EtOH was treated with $Pd(OH)_2/C$ (140 mg) under an $H_2$ atmosphere to yield amine 103. Amine 103 was combined with appropriately deuterated aldehyde 111 in $CH_2Cl_2$ (5 mL), $Na_2SO_4$ and $NaCNBD_3$ to afford 107. A solution of 107 in HCl/MeOH was heated to reflux to afford the free amine 108. The amine 108 in $CH_2Cl_2$ was combined with saturated $Na_2CO_3$ and $H_2O$ followed by appropriately deuterated cyclohexanecarbonyl chloride 109 to produce a compound of Formula II.

Other approaches to synthesizing compounds of the formulae herein can readily be adapted from references cited herein. Variations of these procedures and their optimization are within the skill of the ordinary practitioner.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $Y^1$, $Y^2$, etc.) or not. The suitability of a chemical group in a compound structure for use in the synthesis of another compound is within the knowledge of one of ordinary skill in the art. Additional methods of synthesizing compounds of the formulae herein and their synthetic precursors, including those within routes not explicitly shown in schemes herein, are within the means of chemists of ordinary skill in the art. Methods for optimizing reaction conditions, if necessary minimizing competing by-products, are known in the art. In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier MDL), or internet search engines such as Google® or keyword databases such as the US Patent and Trademark Office text database.

The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Combinations of substituents and variables envisioned by this invention are only those that result in the formation of stable compounds.

The invention further provides a mixture of a compound of this invention and its lighter isotopologues. These mixtures may occur, for instance, simply as the result of an inefficiency of incorporating the isotope at a given position; intentional or inadvertent exchange of protons for deuterium, e.g. exchange of bulk solvent for heteroatom-attached deuterium; or intentional mixtures of pure compounds.

In one embodiment, such mixtures comprise at least about 50% of the heavy atom isotopic compound (i.e., less than about 50% of lighter isotopologues). More specific is a mixture comprising at least 80% of the heavy atom isotopic compound. Even more specific is a mixture comprising 90% of the heavy atom isotopic compound. In one aspect, is a mixture at least about "X" % of the heavy atom isotopic compound (i.e., less than about X % of lighter isotopologues), where X is a number between 0 and 100, inclusive.

Compositions

The invention also provides pyrogen-free compositions comprising an effective amount of a compound of this invention (e.g., including any of the formulae herein), or a pharmaceutically acceptable salt, solvate, or hydrate of said compound; and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Such administration is known to be effective with erectile dysfunction drugs: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

Preferred compositions of this invention are prepared for oral administration, preferably in a tablet form. An example of a preparation of a tablet form useful in the present invention in disclosed PCT publication WO 01/90106.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of the present invention further comprises a second therapeutic agent. The second therapeutic agent includes any compound or therapeutic agent known to have or that demonstrates advantageous properties when administered with a CCR5 modulator, as well as any compound useful in the treatment of HIV infection, any compound useful in the treatment of opportunistic infections, neoplasms and other condition associated with the immune-compromised state caused by AIDS, an immunostimulator, a cytochrome P-450 inhibitor such as a low dosage of ritonavir, or any compound effective to treat pain or inflammation associated with an HIV infection. Such agents are described in detail in PCT publication WO 01/90106, in United States patent publication 20060122220, and are well known in the art. Preferably, the second therapeutic agent is an agent useful in the treatment or prevention of a HIV infection.

Even more preferably the second therapeutic agent that is co-formulated with a compound of this invention is a HIV protease inhibitor, a non-nucleoside reverse transcriptase inhibitor ("NNRTI"), or a nucleoside reverse transcriptase inhibitor ("NRTI").

In some embodiments, any compound of this invention may be co-formulated with multiple second therapeutic agents selected from one or more NNRTIs; one or more NRTIs; and one or more HIV protease inhibitors. In one preferred embodiment, the multiple second therapeutic agents are selected from two different NNRTIs; one HIV protease inhibitor and one NNRTI; and two different NNRTIs and one HIV protease inhibitor. In another embodiment, the second therapeutic agent co-formulated with a compound of this invention is zidovudine/lamivudine ("Combivir®").

In another embodiment, the invention provides separate dosage forms of a compound of this invention and one or more second therapeutic agents that are each associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 300 mg/kg, more preferably 0.01 mg/kg to about 30 mg/kg, more preferably 0.01 mg/kg to about 15 mg/kg. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents referenced above will act synergistically with the compounds of this invention. When this occurs, its will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a subject suffering from or susceptible to a disease that is beneficially treated by maraviroc comprising the step of administering to said subject an effective amount of a compound or a composition of this invention.

Such diseases include HIV infection, a retroviral infection genetically related to HIV, AIDS, inflammatory disease, respiratory disorders (including adult respiratory distress syndrome (ARDS), bronchitis, chronic bronchitis, chronic obstructive pulmonary disease, cystic fibrosis, asthma, emphysema, rhinitis and chronic sinusitis), inflammatory bowel disease (including Crohn's disease and ulcerative colitis), multiple sclerosis, rheumatoid arthritis, graft rejection (in particular but not limited to kidney and lung allografts), endometriosis, type I diabetes, renal diseases, chronic pancreatitis, inflammatory lung conditions and chronic heart failure.

In a preferred embodiment, the method of this invention is used to treat a subject suffering from or suspected of having a HIV infection.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, the above method of treatment comprises the further step of co-administering to said patient one or more second therapeutic agents. The choice of second therapeutic agent may be made from any second therapeutic agent known to be useful for co-administration with maraviroc. Such agents are described in PCT patent publication WO 01/90106, as are the conditions and diseases for which each may be used in conjunction with a compound of this invention.

In a preferred embodiment, a compound of this invention is co-administered with one or more of a HIV protease inhibitor, a non-nucleoside reverse transcriptase inhibitor ("NNRTI"), and a nucleoside reverse transcriptase inhibitor. Included in such an embodiment is the co-administration of more than one second therapeutic agent of each class alone; co-administration of a second therapeutic agent from each of multiple classes; and co-administration of both multiple agents from each class; and multiple agents of different classes. Most preferably, a compound of this invention is co-administered with zidovudine/lamivudine ("Combivir®").

The term "co-administered" as used herein means that the second therapeutic agent may be administered together with a compound of this invention as part of a single dosage form (such as a composition of this invention comprising a compound of the invention and a second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a subject does not preclude the separate administration of that same therapeutic agent, any other second therapeutic agent or any compound of this invention to said subject at another time during a course of treatment. When multiple second therapeutic agents are co-administered, they, too, may be administered as separate dosage forms, single dosage forms or a combination thereof.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of this invention alone or together with one or more of the above-described second therapeutic agents in the manufacture of a medicament, either as a single composition or as separate dosage forms, for treatment or prevention in a subject of a disease, disorder or symptom set forth above.

Another aspect of the invention is a compound of the formulae herein for use in the treatment or prevention in a subject of a disease, disorder or symptom thereof delineated herein.

Diagnostic Methods and Kits

The compounds and compositions of this invention are also useful as reagents in methods for determining the concentration of maraviroc in solution or biological sample such as plasma, examining the metabolism of maraviroc and other analytical studies.

According to one embodiment, the invention provides a method of determining the concentration, in a solution or a biological sample, of maraviroc, comprising the steps of:
  a) adding a known concentration of a compound of Formula I or II to the solution of biological sample;
  b) subjecting the solution or biological sample to a measuring device that distinguishes maraviroc from a compound of Formula I or II;
  c) calibrating the measuring device to correlate the detected quantity of the compound of Formula I or II with the known concentration of the compound of Formula I or II added to the biological sample or solution; and
  d) measuring the quantity of maraviroc in the biological sample with said calibrated measuring device; and
  e) determining the concentration of maraviroc in the solution of sample using the correlation between detected quantity and concentration obtained for a compound of Formula I or II.

Measuring devices that can distinguish maraviroc from the corresponding compound of Formula I or II include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula I or II comprising the steps of contacting the compound of Formula I or II with a metabolizing enzyme source for a period of time and comparing the amount of the compound of Formula I or II with the metabolic products of the compound of Formula I or II after the period of time.

In a related embodiment, the invention provides a method of evaluating the metabolic stability of a compound of Formula I or II in a patient following administration of the compound of Formula I or II. This method comprises the steps of obtaining a serum, urine or feces sample from the patient at a period of time following the administration of the compound of Formula I or II to the subject; and comparing the amount of the compound of Formula I or II with the metabolic products of the compound of Formula I or II in the serum, urine or feces sample.

Diagnostic Methods and Kits

The present invention also provides kits for use to treat a HIV infection. These kits comprise: a) a pharmaceutical composition comprising a compound of this invention or a salt thereof; or a prodrug, or a salt of a prodrug thereof; or a hydrate, solvate, or polymorph thereof, wherein said pharmaceutical composition is in a container; and b) instructions describing a method of using the pharmaceutical composition to treat a HIV infection.

The container may be any vessel or other sealed or sealable apparatus that can hold said pharmaceutical composition.

Examples include bottles, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. Preferably, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

The kit may additionally comprise a memory aid of the type containing information and/or instructions for the physician, pharmacist or subject. Such memory aids include numbers printed on each chamber or division containing a dosage that corresponds with the days of the regimen which the tablets or capsules so specified should be ingested, or days of the week printed on each chamber or division, or a card which contains the same type of information. For single dose dispensers, memory aids further include a mechanical counter which indicates the number of daily doses that have been dispensed and a battery-powered micro-chip memory coupled with a liquid crystal readout and/or audible reminder signal which, for example, reads out the date that the last daily dose has been taken and/or reminds one when the next dose is to be taken. Other memory aids useful in such kits are a calendar printed on a card, as well as other variations that will be readily apparent.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of Compounds 200 and 203

Synthesis of Compounds 200 and 203 was carried out using the general scheme set forth in Scheme 3, above. The details of the synthesis steps are set forth below.

Synthesis of 8-benzyl-8-azabicyclo[3.2.1]octan-3-one 98 A solution of 2,5-dimethoxytetrahydrofuran (95; 22.2 mL, 0.17 mol) in 0.1 M HCl (300 mL) was stirred under reflux conditions for 1 h. The mixture was cooled to 0° C. followed first by the addition of acetone dicarboxylic acid (96; 25g, 0.17 mol), then benzyl amine HCl salt (97; 20.5 g, 0.14 mol), and finally 10% aqueous sodium acetate (95 mL). The resultant mixture was heated to 50° C., stirred for 5 h, then cooled to room temperature and made basic (pH=10) by the addition of 5N NaOH. The basic mixture was washed with $H_2O$ (2×100 mL) and the organic layer was dissolved in 1M HCl (200 mL), washed with $CH_2Cl_2$ (2×100 mL), then made basic with 2M NaOH. The aqueous phase was extracted with EtOAc (3×100 mL) and the combined organic extracts were dried over $MgSO_4$, filtered, and concentrated in vacuo to give pure 98 (17 g, 56%) as a yellow oil.

Synthesis of 8-benzyl-8-azabicyclo[3.2.1]octan-3-one oxime 99 To a solution of 8-benzyl-8-azabicyclo[3.2.1]octan-3-one 98 (17 g, 78 mmol) in ethanol (300 mL), was added hydroxylamine hydrochloride (5.42 g, 78 mmol, 1.0 equiv) followed by pyridine (6.9 mL, 85 mmol, 1.1 equiv). The mixture was heated under reflux conditions for 18 h then was cooled to room temperature, diluted with aqueous $NaHCO_3$, filtered, and concentrated in vacuo. The resulting residue was diluted with $CH_2Cl_2/H_2O$ (1:1, 200 mL), the aqueous phase was extracted with $CH_2Cl_2$ (3×50 mL), and the organic extracts were dried over $MgSO_4$, filtered, and concentrated in vacuo. The crude material was purified by column chromatography (5-10% $MeOH/CH_2Cl_2$) to afford pure 8-benzyl-8-azabicyclo[3.2.1]octan-3-one oxime 99 (15.3 g, 85%).

Synthesis of 8-benzyl-8-azabicyclo[3.2.1]octan-3-amine 100. To a solution of oxime 99 (7.65 g, 33 mmol) in 1-pentanol (130 mL) at 120° C., was added sodium metal (7.6 g, 0.33 mol, 10.0 equiv) portionwise over 2 h. The mixture was stirred and heated under reflux conditions for 5 h, then was cooled to 5° C. The reaction mixture was slowly acidified with 6M HCl to a pH of 2 then was further extracted with 6M HCl (3×100 mL). The aqueous layer was gradually made basic by the addition of 5M NaOH to a pH of 10. The resulting aqueous solution was extracted with EtOAc (3×100 mL) and the combined organic extracts were dried over $MgSO_4$, filtered, and concentrated in vacuo. Purification of the crude material via column chromatography (5-10% $MeOH/CH_2Cl_2$) afforded pure 8-benzyl-8-azabicyclo[3.2.1]octan-3-amine 100 as a solid (2.60 g, 36%).

Synthesis of N-(8-benzyl-8-azabicyclo[3.2.1]octan-3-yl) isobutyramide 101. To a solution of amine 100 (2.70 g, 12.48 mmol) in $CH_2Cl_2$ (13 mL), was added 1M $Na_2CO_3$ (19 mL, 18.72 mmol, 1.5 equiv). The mixture was cooled to 0° C. and isobutyryl chloride (1.6 mL, 14.98 mmol, 1.2 equiv) was added dropwise with stirring over 30 min. The resulting mixture was warmed to room temperature and allowed to stir for 2 h after which time the layers were separated and the aqueous layer was extracted with $CH_2Cl_2$ (3×25 mL). The combined organic layers were washed with 1N NaOH (2×20 mL), then with $H_2O$ (2×20 mL), then dried over $MgSO_4$, filtered, and concentrated in vacuo to yield amide 101 (3.3 g, 93%).

Synthesis of 8-benzyl-3-(3-isopropyl-5-methyl-4H-1,2,4-triazol-4-yl)-8-azabicyclo[3.2.1]octane 102 ($Y^{2a}=Y^{2b}=Y^{2c}=H$). To a solution of amide 101 (3.3 g, 11.58 mmol) in $CHCl_3$ (12 mL) at 0° C., was added pyridine (6.2 mL, 77.59 mmol, 6.7 equiv) with stirring, followed by the dropwise addition of $POCl_3$ (3.3 mL, 35.90 mmol, 3.1 equiv). The mixture was allowed to warm to room temperature, was stirred for 18 h, then concentrated in vacuo as an azeotrope with toluene. The resultant residue was dissolved in $CHCl_3$ (12 mL) before the addition of diisopropylethylamine (6.0 mL, 34.74 mmol, 3.0 equiv) and acetylhydrazine (110; 1.3 g, 17.40 mmol, 1.5 equiv). The reaction mixture was stirred under reflux conditions for 18 h, cooled to room temperature, diluted with saturated $Na_2CO_3$, extracted with $CH_2Cl_2$ (3×25 mL) and the combined organic extracts were concentrated in vacuo. The residue was dissolved in 6M HCl and the mixture stirred under reflux conditions for 18 h. The mixture was made basic by the addition of 5N NaOH, then was extracted with CH$_2$Cl$_2$ (3×25 mL). The combined organic extracts were dried over MgSO$_4$, filtered and concentrated in vacuo. Purification of the crude material via column chromatography (1% NH$_3$ in 5% MeOH/CH$_2$Cl$_2$) afforded the pure triazol product 102 (Y$_{2a-c}$=H) (1.5 g, 40%).

Synthesis of 8-benzyl-3-(3-isopropyl-5-d$_3$-methyl-4H-1,2,4-triazol-4-yl)-8-azabicyclo[3.2.1]octane 102-d$_3$ (Y$_{2a}$=Y$_{2b}$=Y$_{2c}$=D). To a solution of amide 101 (1.80 g, 6.26 mmol) in CHCl$_3$ (6.3 mL) at 0° C., was added pyridine (3.4 mL, 44.94 mmol, 6.7 equiv) with stirring, followed by the dropwise addition of POCl$_3$ (1.8 mL, 19.42 mmol, 3.1 equiv). The mixture was allowed to warm to room temperature, was stirred for 18 h, then concentrated in vacuo as an azeotrope with toluene. The resultant residue was dissolved in CHCl$_3$ (6.3 mL) before the addition of diisopropylethylamine (3.3 mL, 18.78 mmol, 3.0 equiv) and d$_3$-acetylhydrazine 110-d$_3$ (0.72 g, 9.39 mmol, 1.5 equiv). The reaction mixture was stirred under reflux conditions for 18 h, cooled to room temperature, diluted with saturated Na$_2$CO$_3$, extracted with CH$_2$Cl$_2$ (3×25 mL) and the combined organic extracts were concentrated in vacuo. The residue was dissolved in 6M HCl and the mixture stirred under reflux conditions for 8 h. The mixture was made basic by the addition of 5N NaOH, then was extracted with CH$_2$Cl$_2$ (3×25 mL). The combined organic extracts were dried over MgSO$_4$, filtered and concentrated in vacuo. Purification of the crude material via column chromatography (1% NH$_3$ in 5% MeOH/CH$_2$Cl$_2$) afforded the pure 5-d$_3$-methyl triazol product 102-d$_3$ (0.82 g, 40%).

Synthesis of 3-(3-isopropyl-5-methyl-4H-1,2,4-triazol-4-yl)-8-azabicyclo[3.2.1]octane 103 (Y$^{2a}$=Y$^{2b}$=Y$^{2c}$=H). To a solution of the triazole 102 (0.28 g, 0.86 mmol) in EtOH (9 mL) at ambient temperature was added 20 wt % Pd(OH)$_2$/C (140 mg). The mixture was purged with argon then placed under an H$_2$ atmosphere and stirred at ambient temperature for 18 h. The reaction mixture was filtered through a pad of celite, the pad washed with EtOH, and the filtrate was concentrated in vacuo to yield 103 (0.20 g, ~100%).

Synthesis of 3-(3-isopropyl-5-d$_3$-methyl-4H-1,2,4-triazol-4-yl)-8-azabicyclo[3.2.1]octane 103-d$_3$ (Y$^{2a}$=Y$^{2b}$=Y$^{2c}$=D). To a solution of the deuterated triazole 102-d$_3$ (0.23 g, 0.70 mmol) in EtOH (7.0 mL) at ambient temperature was added 20 wt % Pd(OH)$_2$/C (120 mg). The mixture was purged with argon then placed under an H$_2$ atmosphere and stirred at ambient temperature for 18 h. The reaction mixture was filtered through a pad of celite, the pad washed with EtOH, and the filtrate was concentrated in vacuo to yield 103-d$_3$ (0.16 g, 95%).

Synthesis of tert-butyl 3-(3-(3-isopropyl-5-methyl-4H-1,2,4-triazol-4-yl)-8azabicyclo[3.2.1]octan-8-yl)-1-phenyl-3-d$_2$-propylcarbamate 107-d$_2$ (Y$^{1a}$=Y$^{1b}$=D, Y$^{2a}$=Y$^{2b}$=Y$^{2c}$=H). To a solution of amine 103 (0.20 g, 0.86 mmol), and 3-tert-butyl-3-phenylpropyl-1-d$_1$-aldehyde 111 (0.26 g, 1.03 mmol, 1.2 equiv) in CH$_2$Cl$_2$ (5 mL), at room temperature, was added Na$_2$SO$_4$. The mixture was stirred for 15 min followed by the addition of NaCNBD$_3$ (69 mg, 1.03 mmol, 1.2 equiv). The resultant mixture was stirred at room temperature for 15 h, diluted with 10% K$_2$CO$_3$, and extracted with CH$_2$Cl$_2$ (3×20 mL). The combined organic extracts were washed with brine solution, dried over MgSO$_4$, filtered and concentrated in vacuo to afford 107-d$_2$, which was carried on to the next step without purification.

Synthesis of tert-butyl 3-(3-(3-isopropyl-5-d$_3$-methyl-4H-1,2,4-triazol-4-yl)-8azabicyclo[3.2.1]octan-8-yl)-1-phenyl-3-d$_2$-propylcarbamate 107-d$_5$ (Y$^{1a}$=Y$^{1b}$=D, Y$^{2a}$=Y$^{2b}$=Y$^{2c}$=D). To a solution of amine 103-d$_3$ (0.16 g, 0.67 mmol), and aldehyde 111 (0.20 g, 0.81 mmol, 1.2 equiv) in CH$_2$Cl$_2$ (5 mL), at room temperature, was added Na$_2$SO$_4$. The mixture was stirred for 15 min followed by the addition of NaCNBD$_3$ (54 mg, 0.81 mmol, 1.2 equiv). The resultant mixture was stirred at room temperature for 15 h, diluted with 10% K$_2$CO$_3$, and extracted with CH$_2$Cl$_2$ (3×20 mL). The combined organic extracts were washed with brine solution, dried over MgSO$_4$, filtered and concentrated in vacuo to afford 107-d$_5$ which was carried on to the next step without purification.

Synthesis of 3-(3-(3-isopropyl-5-methyl-4H-1,2,4-triazol-4-yl)-8azabicyclo[3.2.1]octan-8-yl)-1-phenyl-d$_2$-propan-1-amine 108-d$_2$ (Y$^{1a}$=Y$^{1b}$=D, Y$^{2a}$=Y$^{2b}$=Y$^{2c}$=H). A solution of 107-d$_2$ (0.39 g, 0.86 mmol) in 1.25M HCl/MeOH (7 mL, 10 equiv) was heated to refluxing temperature and stirred for 5 min. The solution was allowed to cool to room temperature, stirred an additional 1.5 h, and then was concentrated in vacuo. The residue was dissolved in CH$_2$Cl$_2$ (10 mL) and stirred with saturated Na$_2$CO$_3$ solution. The layers were separated and the aqueous layer was extracted with CH$_2$Cl$_2$ (3×20 mL). The combined organic extracts were washed with brine solution, dried over MgSO$_4$, filtered and concentrated in vacuo to afford the free amine 108-d$_2$ (0.32 g, ~100%).

Synthesis of 3-(3-(3-isopropyl-5-d$_3$-methyl-4H-1,2,4-triazol-4-yl)-8-azabicyclo[3.2.1]octan-8-yl)-1-phenyl-3-d$_2$-propan-1-amine 108-d$_5$ (Y$_{1a}$=Y$_{1b}$=D, Y$_{2a}$=Y$_{2b}$=Y$_{2c}$=D). A solution of 107-d$_5$ (0.32 g, 0.67 mmol) in 1.25M HCl/MeOH (5.4 mL, 10 equiv) was heated to refluxing temperature and stirred for 5 min. The solution was cooled to room temperature, stirred an additional 1.5 h, and then concentrated in vacuo. The residue was dissolved in CH$_2$Cl$_2$ (10 mL) and stirred with saturated Na$_2$CO$_3$ solution. The layers were separated and the aqueous layer was extracted with CH$_2$Cl$_2$ (3×20 mL). The combined organic extracts were washed with brine solution, dried over MgSO$_4$, filtered and concentrated in vacuo to afford the free amine 108-d$_5$ (0.25 g, ~100%).

Synthesis of 4,4-difluoro-N-(3-(3-(3-isopropyl-5-methyl-4H-1,2,4-triazol-4-yl)-8-azabicyclo[3.2.1]octan-8-yl)-1-phenyl-3-d$_2$-propyl)cyclohexanecarboxamide (Compound 200). To a stirred solution of amine 108-d$_2$ (0.32 g, 0.86 mmol) in CH$_2$Cl$_2$ (4 mL), was added saturated Na$_2$CO$_3$ (3.4 mL) and H$_2$O (3.0 mL), followed by cyclohexanecarbonyl chloride 109 in toluene (1.3 mL of 1M stock solution, 1.30 mmol, 1.5 equiv). The reaction mixture was stirred for 12 h at room temperature, then was diluted with H$_2$O (5 mL) and CH$_2$Cl$_2$ (5 mL). The pH of the resultant aqueous phase was measured at 11. The aqueous layer was extracted with CH$_2$Cl$_2$ (3×20 mL) and the combined organic extracts were washed with 0.5M NaOH, then with H$_2$O, dried over MgSO$_4$, filtered and concentrated in vacuo. Purification on SiO$_2$ (2.5%-5% MeOH/DCM) afforded 0.27 g (60%) of the desired product, Compound 200. $^1$H-NMR (300 MHz, CDCl$_3$): δ 1.38 (d, J=8.2, 6H), 1.58-2.20 (m, 18H), 2.45 (d, J=9.7, 1H), 2.50 (s, 3H), 2.95-3.00 (m, 1H), 3.36-3.40 (m, 2H), 4.24-4.35 (m, 1H), 5.13-5.14 (m, 1H), 6.51-6.58 (m, 1H), 7.27-7.49 (m, 5H). HPLC (method: 150 mm C18-RP column—gradient method 5-95% ACN; Wavelength: 254 nm): retention time: 3.10 min. MS (M+H$^+$): 516.0.

Synthesis of 4,4-difluoro-N-(3-(3-(3-isopropyl-5-d$_3$-methyl-4H-1,2,4-triazol-4-yl)-8-azabicyclo[3.2.1]octan-8-yl)-1-phenyl-3-d$_2$-propyl)cyclohexanecarboxamide (Compound 203). To a stirred solution of amine 108-d$_5$ (Y$_{1a-b}$=D, Y$_{2a-c}$=D) (0.25 g, 0.67 mmol) in CH$_2$Cl$_2$ (3 mL), was added saturated Na$_2$CO$_3$ (2.7 mL) and H$_2$O (2.0 mL), followed by cyclohexanecarbonyl chloride 109 in toluene (1.0 mL of 1M stock solution, 1.0 mmol, 1.5 equiv). The reaction mixture was stirred for 12 h at room temperature, then was diluted with H$_2$O (5 mL) and CH$_2$Cl$_2$ (5 mL). The pH of the resultant aqueous phase was measured at 11. The aqueous layer was extracted with $CH_2Cl_2$ (3×20 mL) and the combined organic extracts were washed with 0.5M NaOH, then with $H_2O$, dried over $MgSO_4$, filtered and concentrated in vacuo. Purification on $SiO_2$ (2.5%-5% MeOH/DCM) afforded 0.18 g (50%) of the desired product, Compound 203. $^1$H-NMR (300 MHz, $CDCl_3$): δ 1.37 (d, J=7.0, 3H), 1.38 (d, J=6.7, 3H), 1.59-2.26 (m, 18H), 2.46-2.49 (m, 1H), 2.94-3.01 (m, 1H), 3.38 (dd, $J_1$=13.8, $J_2$=3.0, 2H), 4.26-4.30 (m, 1H), 5.10-5.15 (m, 1H), 6.74 (d, J=7.3, 1H), 7.27-7.49 (m, 5H). HPLC (method: 150 mm C18—RP column—gradient method 5-95% ACN; Wavelength: 254 nm): retention time: 2.78 min. MS (M+H$^+$): 518.0.

Example 2
Evaluation of Metabolic Stability in Human Microsomes

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay. The metabolic stability of compounds of Formula I was tested using pooled liver microsomal incubations. Full scan LC-MS analyses were then performed to detect major metabolites. Samples of the test compounds, exposed to pooled human liver microsomes, were analyzed using HPLC-MS (or MS/MS) detection. For determining metabolic stability, multiple reaction monitoring (MRM) was used to measure the disappearance of the test compounds. For metabolite detection, Q1 full scans were used as survey scans to detect the major metabolites.

Experimental Procedures. Human liver microsomes are obtained from a commercial source (e.g., XenoTech, LLC (Lenexa, Kans.)). The incubation mixtures are prepared as follows:

| Reaction Mixture Composition | |
|---|---|
| Liver Microsomes | 1.0 mg/mL |
| NADPH | 1 mM |
| Potassium Phosphate, pH 7.4 | 100 mM |
| Magnesium Chloride | 10 mM |
| Test Compound | 1 μM. |

Incubation of Test Compounds with Liver Microsomes: The reaction mixture, minus cofactors, was prepared. An aliquot of the reaction mixture (without cofactors) was incubated in a shaking water bath at 37° C. for 3 minutes. Another aliquot of the reaction mixture was prepared as the negative control. The test compound (Compound 200 or Compound 203) was added into both the reaction mixture and the negative control at a final concentration of 1 μM. Six duplicate reactions were run for each compound tested. An aliquot of the reaction mixture was prepared as a blank control, by the addition of plain organic solvent (not the test compound). The reaction was initiated by the addition of cofactors (not into the negative controls), and then incubated in a shaking water bath at 37° C. Aliquots (200 μL) were withdrawn in triplicate at 0, 5, 10, 20, 30, and 60 minutes and combined with 800 μL of ice-cold 50/50 acetonitrile/$dH_2O$ to terminate the reaction. The positive controls, testosterone and propranolol, were run simultaneously with the test compounds in separate reactions.

Figure 1:
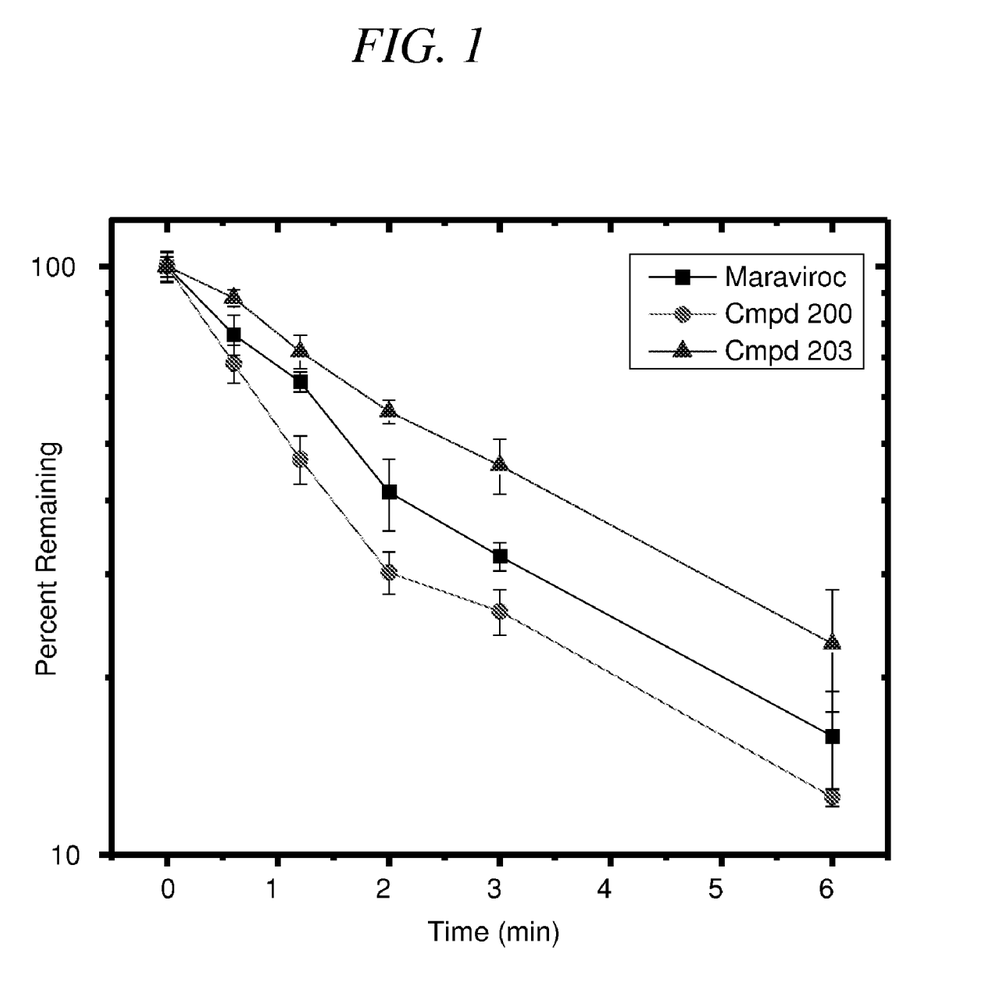
FIG. 1 depicts the metabolic stability of compounds of Formula I as compared to maraviroc in human liver microsomes.

All samples were analyzed using LC-MS (or MS/MS). An LC-MRM-MS/MS method was used for metabolic stability. Also, Q1 full scan LC-MS methods were performed on the blank matrix and the test compound incubation samples. The Q1 scans served as survey scans to identify any sample unique peaks that might represent the possible metabolites. The masses of these potential metabolites can be determined from the Q1 scans. The results of this assay are shown in FIG. 1.

Example 3

SUPERSOMES™ Assay

Various human cytochrome P450-specific SUPERSOMES™ are purchased from Gentest (Woburn, Mass., USA). A 1.0 mL reaction mixture containing 25 pmole of SUPERSOMES™, 2.0 mM NADPH, 3.0 mM MgCl, and 1 λM of a compound of Formula I or II in 100 mM potassium phosphate buffer (pH 7.4) was incubated at 37° C. in triplicate. Positive controls contain 1 μM of Maraviroc instead of a compound of formula I. Negative controls used Control Insect Cell Cytosol (insect cell microsomes that lacked any human metabolic enzyme) purchased from GenTest (Woburn, Mass., USA). Aliquots (50 μL) are removed from each sample and placed in wells of a multi-well plate at various time points (e.g., 0, 2, 5, 7, 12, 20, and 30 minutes) and to each aliquot is added 50 μL of ice cold acetonitrile with 3 μM haloperidol as an internal standard to stop the reaction.

Plates containing the removed aliquots are placed in −20° C. freezer for 15 minutes to cool. After cooling, 100 μL of deionized water is added to all wells in the plate. Plates are then spun in the centrifuge for 10 minutes at 3000 rpm. A portion of the supernatant (100 μL) is then removed, placed in a new plate and analyzed using Mass Spectrometry.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

I claim:

1. A compound of formula II:

(II)

or a salt, thereof; wherein:
each Y is independently selected from hydrogen or deuterium;
each Z is independently selected from hydrogen or deuterium; and
wherein each $Y^1$ is deuterium and each $Y^2$ is deuterium.

2. The compound of claim 1, wherein each Z bound to the same carbon atom is the same.

3. The compound of claim 2, wherein each Z is hydrogen.

4. The compound of claim 2, wherein each member of at least one pair selected from $Z^1$ and $Z^2$; $Z^3$ and $Z^4$; $Z^5$ and $Z^6$; or $Z^7$ and $Z^8$ is simultaneously deuterium.

5. The compound of claim 1, selected from any one of compounds set forth in the table below:

| Cmpd | $Y^{1a}$ | $Y^{1b}$ | $Y^{2a}$ | $Y^{2b}$ | $Y^{2c}$ | $Z^1$ | $Z^2$ | $Z^3$ | $Z^4$ | $Z^5$ | $Z^6$ | $Z^7$ | $Z^8$ |
|---|---|---|---|---|---|---|---|---|---|---|---|---|---|
| 203 | D | D | D | D | D | H | H | H | H | H | H | H | H |
| 206 | D | D | D | D | D | D | D | D | D | D | D | D | D |
| 209 | D | D | D | D | D | D | D | H | H | H | H | D | D |
| 212 | D | D | D | D | D | H | H | D | D | D | D | H | H. | or a pharmaceutically acceptable salt thereof.

6. The compound

Compound 203 or a pharmaceutically acceptable salt, thereof.

7. The compound of claim 1, wherein any atom not designated as deuterium is present at its natural isotopic abundance.

8. A pyrogen-free composition comprising a compound of claim 1 or a pharmaceutically acceptable salt, thereof; and an acceptable carrier.

9. The composition of claim 8 formulated for pharmaceutical administration, wherein the carrier is a pharmaceutically acceptable carrier.

* * * * *